(12) United States Patent
Usui (10) Patent No.: US 6,441,345 B1
(45) Date of Patent: Aug. 27, 2002

(54) WAX SPATULA APPARATUS

(75) Inventor: Masaki Usui, Kyoto (JP)

(73) Assignee: Denken Co., Ltd., Kyoto (JP)

( * ) Notice: Subject to any disclaimer, the term of this patent is extended or adjusted under 35 U.S.C. 154(b) by 0 days.

(21) Appl. No.: 09/851,092

(22) Filed: May 9, 2001

(30) Foreign Application Priority Data

May 12, 2000 (JP) ........................................ 2000-140082

(51) Int. Cl.⁷ ................................................ H05B 3/20
(52) U.S. Cl. ........................................ 219/228; 219/227
(58) Field of Search ................................ 219/228, 240, 219/241, 229, 227, 231, 251, 252; 228/51, 55; 30/140

(56) References Cited

U.S. PATENT DOCUMENTS 4,822,979 A * 4/1989 deKam ........................ 219/241
5,747,778 A * 5/1998 Liu .............................. 219/506

* cited by examiner

Primary Examiner—Teresa Walberg
Assistant Examiner—Vinod D Patel (74) Attorney, Agent, or Firm—Wenderoth, Lind & Ponack, L.L.P.

(57) ABSTRACT

An electrically-heated wax spatula apparatus for use in molding and preparing wax models for investment casting in the field of dental prostheses and the field of metal work based on casting, and more particularly a wax spatula apparatus wherein the temperature of its spatula portion for wax-molding work can be adjusted immediately during use. The wax spatula apparatus comprises a spatula body, which is provided with a heating portion accommodating an electric heating element and a temperature sensor at the front end of the grip portion thereof and a wax-molding spatula portion installed in the heating portion, and a temperature controller for controlling the temperature of the spatula portion depending on a temperature signal from said temperature sensor of said heating portion, wherein the temperature controller comprises temperature-setting means capable of independently setting the temperature of the spatula portion at a plurality of temperature levels, and preset temperature selection means for selecting the preset temperature levels determined by said temperature-setting means, and the temperature-setting means is a temperature-setting switch disposed at the front end of the grip portion so as to be operable with a fingertip, whereby the temperature of the spatula portion is changed and adjusted immediately by operating the temperature-setting switch with a fingertip during wax-molding work.

22 Claims, 4 Drawing Sheets

WAX SPATULA APPARATUS

BACKGROUND OF THE INVENTION

1. Field of the Invention

The present invention relates to an electrically-heated wax spatula apparatus for use in molding and preparing wax models for investment casting in the field of dental prostheses and the field of metal work based on investment casting, and more particularly to a wax spatula apparatus wherein the temperature of its spatula portion for wax-molding work can be adjusted immediately during use.

2. Prior Art

A dental wax spatula apparatus is a wax-molding device for forming or preparing wax models for dental plates, crowns, etc. in a process wherein these dental parts are molded simultaneously from dental alloy materials by an investment casting technique, such as the lost-wax process. The wax spatula apparatus is also used frequently to shape wax models for metal work products made by the centrifugal casting process. Conventional wax spatula apparatuses are classified into a type that is used while being heated by a burner and another type in which the apparatuses are provided with a heater so as to generate heat by itself.

A process of molding a wax model by using a wax spatula apparatus includes an operation step wherein the heated spatula portion of the spatula apparatus is put into wax (material) in order to melt the wax, a certain amount of the wax is cut off, and the wax is piled up on a predetermined base. Furthermore, the process includes another operation step wherein the wax piled up on the base is softened and molded into a desired shape by partially shaving and moving the wax or by adding a further amount of the wax. Moreover, the process includes still another operation step wherein the surface of the molded wax is smoothened or provided with fine patterns. The spatula portion is required to heated at an optimum temperature at each of the operation steps. It is therefore necessary to quickly change and finely adjust the temperature of the wax in the range of the melting temperature to softening temperature of the wax.

Although conventional electrically-heated wax spatula apparatuses are publicly known, they are not necessarily satisfactory in temperature control. In addition, the spatula portion of such a wax spatula apparatus is required to be replaced with another spatula portion having a shape suited for each of the above-mentioned operation steps. The replacement of the spatula portions makes it difficult to quickly redo temperature control.

There has been known a type of spatula apparatus having an electrically resistant gap, made of metal and being somewhat electrically conductive, formed to divide its spatula portion into two half tips in its width direction, wherein the gap between the tips of the two halves is short-circuited with a heating resistor, and electric power is applied to the halves to heat the resistor (see Japanese Patent Publication No. 7-15006, for example). Although this type of spatula apparatus has an advantage of quick thermal response since the heating portion is short-circuited through the gap at the tip of the spatula portion, it has a difficulty in accurately detecting the temperature of the tip. In other words, current or power supply time has to be adjusted manually, then roughly controlling the temperature of the spatula portion to an temperature required each time the spatula portion is used for wax-molding work.

A modified electrically-heated spatula apparatus invented by the applicants of the present invention has been disclosed in Japanese Patent Publication 10-108872. This spatula apparatus is provided with a heating portion having a ceramic tube with a small electric heating element and a small temperature sensor inserted therein, which heating portion is secured to the tip of the grip portion of the spatula apparatus. Some spatula portions which are formed of a metal spatula in the shapes of plate, knife, spear, needle, and the like, can be exchangeably attached to the heating portion at the tip of the grip portion. Furthermore, the spatula portion can be heated to a desired temperature by thermal conduction from the electric heating element capable of being controlled at two or more levels of preset temperature. This thermally controlled spatula portion have favorably been used to heat and mold wax material.

This spatula apparatus is provided with a temperature controller that controls electric power supplied to the electric heating element while measuring the actual temperature of the spatula portion by using the temperature sensor so that the temperature at the spatula portion can be set at least at two or more levels. The spatula apparatus is also provided with independent temperature selection means for setting temperatures, such as a footswitch or hand switch.

This conventional apparatus has an advantage of being capable of facilitating wax-molding work by setting temperatures at multiple levels by using the temperature selection means. Since the temperature selection means can set two or more temperature levels, the apparatus has an advantage of adjusting the temperature of the spatula portion to a value best suited for each step of spatula operations as described above. In a course of wax work, for example, first, the temperature of the spatula portion is set at a value higher than the melting temperature of wax, and this temperature is used for scooping up a small amount of wax from a wax lump sequentially with said spatula portion and placing it on an object wax model. Then, the temperature of the spatula portion is set at another value lower than the wax melting temperature but higher than the wax softening temperature, and this temperature is used for precisely sculpturing the surfaces of the wax model.

However, in the case of the conventional spatula apparatus, a footswitch or a hand switch have been used to set the temperature of the spatula portion. Although the footswitch or the hand switch can be operated at each change of the preset temperature of the spatula portion during the wax-molding work, the temperature cannot be changed as promptly as is expected, or wax-molding work is not necessarily carried out efficiently; therefore, the operability of the apparatus is unsatisfactory. In addition, since other apparatuses than the spatula apparatus have also been operated frequently by using footswitches in the working environments of dental technicians, the apparatuses may be involved in a danger of being operated improperly.

Furthermore, the so-called cone technique is used to make wax models for artificial teeth. This is an advanced and delicate technique wherein a melted wax lump is solidified and raised like a hone while being cooled by blowing breaths on it delicately when a front tooth or the cusp portion of a molar tooth is molded. A conventional burner-type spatula is suited for this operation since the spatula is cooled spontaneously at an appropriate cooling speed during use. However, in the case of the electrically-heated spatula, its temperature is required to be lowered intentionally. For this purpose, the operator has no choice but to turn off supply power to the electric heating element of the spatula by manually operating the control panel or the above-mentioned footswitch by moving the operator's hand or foot during wax-molding work. This operation is troublesome for the operator since the operator is conducting delicate wax-molding work with both hands.

DISCLOSURE OF THE INVENTION

Accordingly, an object of the present invention is to provide a wax spatula apparatus capable of carrying out delicate temperature adjustment at a spatula portion required for wax-molding work and also capable of lowering and raising the temperature of the spatula portion quickly and accurately by simple human operation.

Another object of the present invention is to accomplish the setting of the temperature of the spatula portion and the controlling of electric power supplied to the electric heating element of the spatula portion required for the setting by using only a fingertip of the hand gripping the spatula, thereby to eliminate the above-mentioned troublesome hand or foot operation.

In the present invention, a temperature-setting switch of temperature-setting means is disposed on a grip portion of the spatula body, and the temperature of the spatula portion is raised or lowered to any of preset values of temperature by operating the above-mentioned switch with a fingertip.

The spatula apparatus in accordance with the present invention comprises a spatula body, which is provided with a heating portion accommodating an electric heating element and a temperature sensor at the front end of the grip portion thereof and a wax-molding spatula portion installed in the heating portion, and a temperature controller for controlling the temperature of the spatula portion by supplying electric power to the electric heating element of the heating portion and by controlling the electric power depending on a temperature signal from the temperature sensor of the heating portion. The temperature controller comprises preset temperature selection means capable of independently selecting a plurality of temperature levels and temperature-setting means capable of setting the temperature of the spatula portion at a selected temperature level. The temperature-setting means includes the temperature-setting switch. By operating the switch, the preset temperature of the spatula portion is raised or lowered to a new, desired temperature value. The temperature controller quickly adjusts the temperature of the spatula portion to the newly preset temperature value by heating or cooling the spatula portion.

In the present invention, the temperature-setting switch is secured to the grip portion of the spatula body so as to be operable with a fingertip. With this configuration, the temperature of the spatula portion can be changed and adjusted by operating the switch easily and quickly during wax-molding work.

The preset temperature selection means is intended to select one of two, three or more temperature levels. The selection switch of the preset temperature selection means is preferably installed in the temperature controller. With this configuration, the selection switch is used to select preset temperature levels so that the temperature of the spatula portion can be switched from a temperature level to another temperature level immediately. Furthermore, the setting of the preset temperature of the spatula portion at the temperature level selected by the temperature-setting switch secured to the grip portion is changed to adjust the temperature of the spatula portion. As a result, the operator can adjust the temperature of the spatula portion in a required range by performing only switch selection. The efficiency of work can thus be improved.

EMBODIMENT OF THE INVENTION

The wax spatula apparatus in accordance with the present invention basically comprises a wax spatula body and a temperature controller. The wax spatula body comprises a grip portion, a heating portion accommodating an electric heating element and a temperature sensor at the front end of the grip portion, and a wax-molding spatula portion removably attached to the heating portion.

First, the heating portion of the wax spatula body comprises a metal sheath secured to the grip portion thereof so that the front end of the metal sheath projects from the grip portion and a ceramic insulator fitted into the front end of the sheath. The ceramic insulator may be a cylinder having a plurality of small through holes to support an electric heating element and a temperature sensor. It is desired that the electric heating element, which may preferably be an electric heating wire, is passed through one or more of the small holes and that the temperature sensor, which may preferably have the shape of a wire, may be passed through the other of the small holes. The lead wires of the electric heating wire and the lead wires of the temperature sensor are passed through the metal sheath to the rear end of the wax spatula body and connected to a temperature controller as described later.

The ceramic insulator may be a sinter of an electrically-insulating ceramic material having high thermal conductivity, such as alumina, aluminum nitride and silica. The insulator may be preferably be formed beforehand into a pillar or cylindrical shape in particular. The above-mentioned through holes are formed in parallel with the longitudinal direction of the pillar. The ceramic insulator is inserted into the front end of the metal sheath and secured thereto.

The calorific value of the electric heating element should have only approximately 10 to 15 W to raise the temperature of the wax spatula. The heating temperature of the electric heating element should be 200° C. or less because the melting temperature of wax is usually approximately 150° C. Hence, a nichrome wire or other resistance wires having the shape of a wire, ribbon, or tape may be used as the electric heating element.

A thermocouple having the shape of a wire, such as an alumel-chromel thermocouple (K thermocouple), may be used for the temperature sensor. A platinum resistance wire may also be used for the temperature sensor.

The spatula portion is removably attached to the front end of the metal sheath of the heating portion. This spatula portion is made of metal and has a cylindrical socket and a wax-molding portion having a desired shape and integrated with the front end of the socket. The cylindrical socket is fitted around the metal sheath disposed at the front end of the spatula body to connect the spatula portion to the spatula body. Spatula portions having various shapes, such as a needle, rod, pan, spatula, knife, etc. are prepared depending on the shape of a wax mold and wax-molding work. These spatula portions are replaceable by detaching the socket of the spatula portion from the metal sheath during wax-molding work.

The grip portion should only have an outer diameter and a length that can be gripped and operated easily with the hand of the operator. Hence, the grip portion may have the shape of a rod, shaft or pipe, and is preferably formed of plastic or rubber material to attain thermal insulation.

As describe above, the metal sheath having the heating portion at its front end is secured to the grip portion so as to project to the front end. In addition, a temperature-setting switch for temperature-setting means is disposed at the front end of the grip portion so as to be operable with a fingertip.

Furthermore, the lead wires of the electric heating wire, the lead wires of the temperature sensor and the lead wires of the temperature-setting switch are passed from the metal sheath of the heating portion through the inside of the grip portion and connected to the cord of the temperature controller.

The temperature controller is used to set the temperature of the heating portion in advance or during operation and to supply electric power to the heating element, thereby to heat the heating portion. Furthermore, the temperature controller is used to adjust the electric power depending on the temperature signal detected by the temperature sensor, thereby to control the temperature of the heating element to a preset temperature.

The temperature controller comprises temperature-setting means for setting the temperature of the heating portion at each of a plurality of temperature levels and preset temperature selection means for selecting a preset temperature signal supplied from the temperature-setting means. The temperature controller further comprises comparison means for comparing selected temperature data from the selection means with actual temperature data from the temperature sensor and for output ting a comparison signal and an electric power control portion for controlling electric power supplied to the electric heating wire by the comparison means.

In this apparatus, the temperature of the tip of the spatula (spatula portion) can be set at least at two levels, preferably at three or four levels. The temperature selection means selects one of the temperature levels, and the temperature controller adjusts the temperature of the spatula portion at the preset temperature corresponding to the selected temperature level. In this way, several temperature levels usually required for wax-molding work are made available, and the preset temperature selection means is operated as necessary. Hence, the preset temperature corresponding to one of the temperature levels is compared with the measured temperature of the spatula portion, and the temperature of the spatula portion can be changed to the temperature level.

The temperature-setting means is used to change the setting of the preset temperature corresponding to the temperature level selected by the preset temperature selection means. Each time the preset temperature is changed and reset by the temperature-setting means, the newly preset temperature is compared with the measured temperature of the spatula portion, and temperature control is carried out so that the temperature of the spatula portion reaches the newly preset temperature. As a result, the temperature of the spatula portion can be controlled to a desired preset temperature.

This temperature controller can be made in various types, such as a type using analog circuits, a type using digital circuits, a type using a microcomputer capable of performing numerically control, etc.

In the case of the controller using a microcomputer, the microcomputer may be used as the comparison means, and a digital input device may be used as the temperature-setting means, which is capable of inputting preset temperature values to the microcomputer, then, selected preset temperature data being stored in a memory. A measured temperature output signal from the temperature sensor is input to the microcomputer after A/D conversion, and compared with preset temperature data as necessary. The comparison output signal of the microcomputer is output to the power control portion. The power control portion controls the electric power supplied to the electric heating wire, whereby the temperature of the heating portion is maintained near the selected preset temperature.

In the computer control, a plurality of temperature levels have been set and recorded in the memory, and a temperature value has been preset for each level. When one of the temperature levels is selected by the preset temperature selection means, the central processing unit (CPU) of the computer refers to the preset temperature corresponding to the selected temperature level, and compares the preset temperature with the measured temperature data. The central processing unit then controls the power control portion in accordance with the comparison data. The selection switch (panel switch) on the operation panel of the temperature controller is usually used as the preset temperature selection means.

The temperature-setting means includes the temperature-setting switch. Each time the preset temperature corresponding to a selected temperature level is reset by the temperature-setting switch, the newly preset temperature data is input to the computer and stored in the memory. At the same time, the data is referred to and compared with the measured temperature voltage output data from the temperature sensor, and electric power to the heating portion is controlled depending on the comparison data as described above. In this way, the temperature of the heating portion, that is, the temperature of the spatula portion, can be made close to the preset temperature immediately. Hence, the operator can carry out delicate temperature control as desired. As a result, by selecting a temperature level different from the current temperature level by the preset temperature selection means, the operator can change the temperature of the heating portion to the preset temperature corresponding to the selected temperature level. Furthermore, the preset temperature corresponding to the temperature level can be set as necessary by using the temperature-setting means. Hence, the preset temperature corresponding to the level can be fine adjusted. In this way, the temperature of the spatula portion can be fine changed sequentially to a temperature value required or best suited for wax-molding work.

The preset temperature set by the temperature-setting means may be set continuously or may be set at intervals of 1° C. or 3° C. to 5° C.

In the present invention, the temperature-setting switch of the temperature-setting means is disposed on the grip portion so as to be operable with a fingertip. By operating the temperature-setting switch with a fingertip, the preset temperature data of the temperature-setting means is changed and recorded as newly preset temperature data sequentially. Hence,. the operator can carry out fine adjustment as described above by operating the temperature-setting switch by using a fingertip of his or her hand holding the grip portion, such as the tip of his or her index finger.

In the present invention, the temperature of the spatula portion can be set at a plurality of temperature levels. When two levels are used for example, the higher temperature level of the spatula portion at the time when wax is piled up with the spatula (usually, a temperature slightly higher than the melting point of wax) and the lower temperature level at the time when the surface of wax is molded (usually, a temperature lower than the melting point of wax) can be determined as the two temperature levels, for example. With this setting, temperature adjustment convenient for wax-molding work can be accomplished by operating the setting temperature selection means during the use of the spatula apparatus. In addition, fine temperature adjustment can be attained by finely resetting the high preset temperature levels sequentially by using the temperature-setting means, Furthermore, the cone technique used to make wax models can be realized very easily by using the spatula apparatus of the present invention. The spatula portion making contact with a raised wax hone to carry out molding can be cooled easily by simply operating the temperature-setting switch with an index finger. For this reason, the spatula apparatus in accordance with the present invention is suited for the cone technique.

EMBODIMENT

Figure 4:
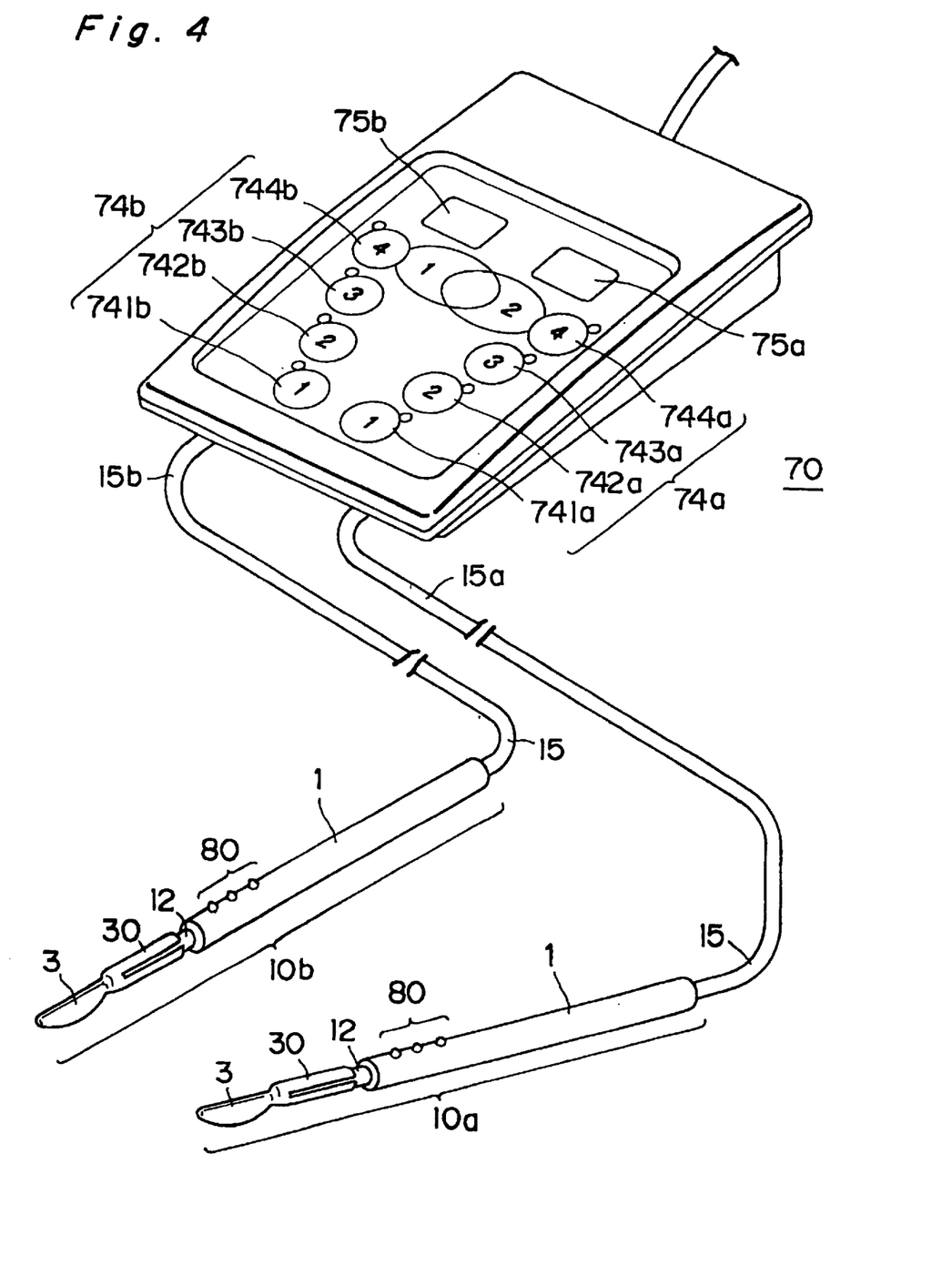
FIG. 4 is an external view showing the wax spatula apparatus in accordance with the embodiment of the present invention.

FIG. 4 is an external view showing a wax spatula apparatus in accordance with an embodiment of the present invention. This apparatus comprises a spatula body 10 and a temperature controller 70. In the spatula body 10, the socket 30 of a spatula portion 3 is fitted around a heating portion 12 secured to the tip of the front end 13 of a grip portion 1. In this embodiment, two spatula bodies 10a and 10b are connected to the temperature controller 70 so as to be usable.

Figure 1A:
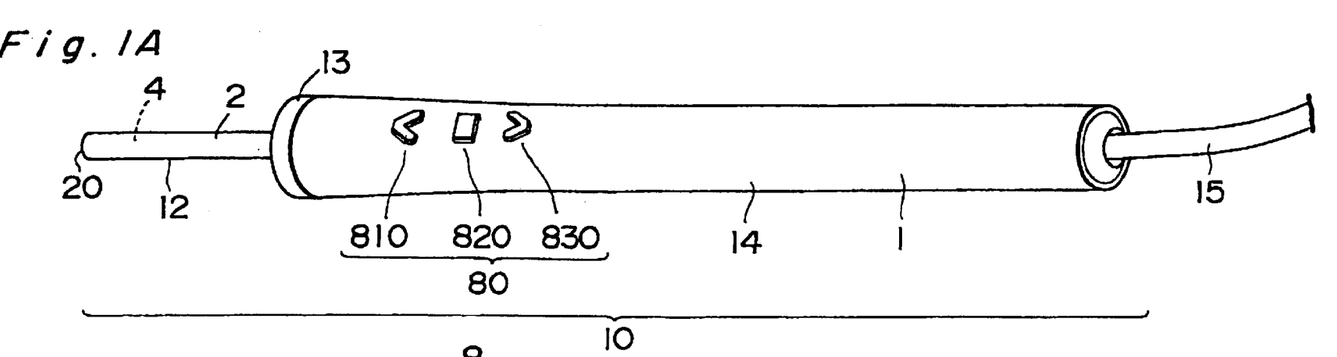
FIG. 1A is a perspective view showing the structure of a wax spatula body in accordance with an embodiment of the present invention.

FIG. 1A is an external view showing the spatula, body 10. The grip portion 1 of the spatula body 10 has the shape of a shaft. A metal sheath 2 projects from the front end of the grip portion 1 so as to be nearly coaxial therewith. A cord 15 only for lead wires is connected to the rear end of the grip portion 1. The push operation portion 80 (810, 820 and 830) of a temperature-setting switch 8 is disposed on the front-end side of the grip portion 1. The push operation portion 80 is positioned where the operator can push the temperature-setting switch 8 while holding the grip portion 1 with a hand.

Figures 1B, 1C:
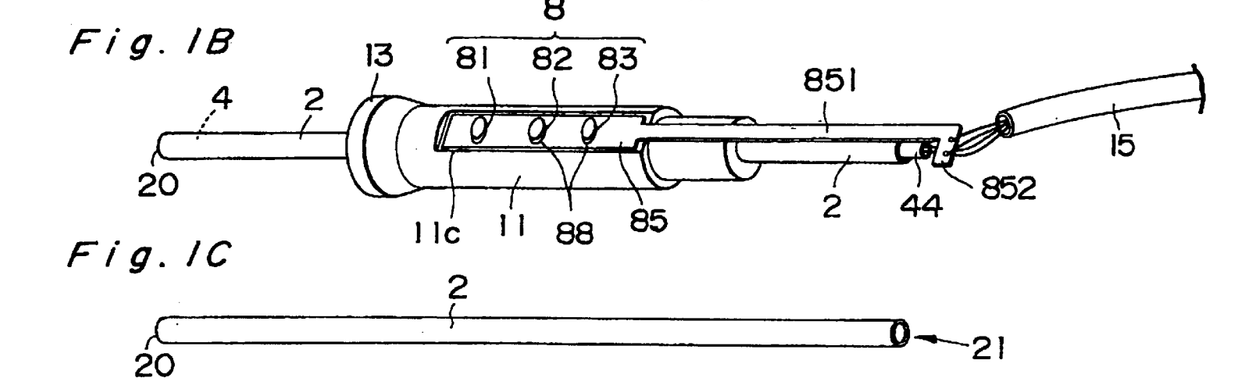
FIG. 1B is a view showing the structure of the body of the grip portion of the wax spatula in accordance with the embodiment of the present invention.
FIG. 1C is a view showing the sheath of the wax spatula in accordance with the embodiment of the present invention.
Figure 1D:
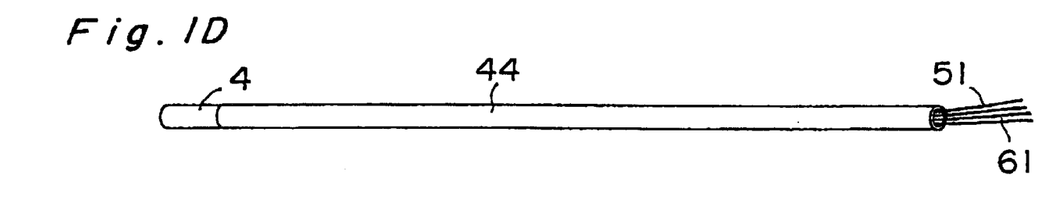
FIG. 1D is a view showing the heating portion of the wax spatula in accordance with the embodiment of the present invention.

The metal sheath 2, shown in FIG. 1C and having a closed front end 20 and an open rear end 21, passes through the spatula body 10 so as to be positioned centrally in the axial direction thereof. The heating portion 12 is inserted into the front end of the metal sheath 2. In the heating portion 12, an electric heating element and a temperature sensor are accommodated in a ceramic insulator 4, and their lead wires are inserted into a sturdy flexible protection tube 44 so as to be protected as shown in FIG. 1D. The protection tube 44 can be formed of a heat-resistant synthetic resin, such as a fluorine resin.

The metal sheath 2 is inserted into the body 11 of the grip portion 1 and secured thereto as shown in FIG. 1B. The body 11 of the grip portion 1, cylindrical in shape, is provided with a temperature-setting switch 8 on its outer periphery and has an expanded portion 13 at its front end. The outer periphery of the body 11 behind the expanded portion 13 is covered with a protection cover 14 formed of tubular soft rubber as shown in FIG. 1A.

Referring to FIG. 1B, the temperature-setting switch B comprises small switches 88, three in number in the case of this embodiment, on a narrow printed-circuit board 85 that is soft and flexible. Wires printed on the printed-circuit board form a switch circuit as will be described later referring-to FIG. 3. The temperature-setting switch 8 formed on the printed-circuit board is secured to an outer flat portion 11c obtained by forming a part of the outer periphery of the body 11 of the grip portion 1 into a flat face. The printed lead wires from the temperature-setting switch 8 are extended along the lead-out portion 851 of the printed-circuit board 85 and connected to the lead wires of the cord 15 at a printed-circuit board connection portion 852.

The body 11 of the grip portion 1 including the temperature-setting switch 8 is covered with the above-mentioned protection cover 14 formed of soft rubber. However, the small switches 88 can be operated by pushing the push operation portion 80 (810, 820 and 830) of the protection cover directly above the small switches (81, 82 and 83) of the temperature-setting switch 8. Marks corresponding to the functions of the small switches 88 should preferably be placed at the push operation portion 80 (810, 820 and 830) of the protection cover to attain convenient operation.

Figure 2A:
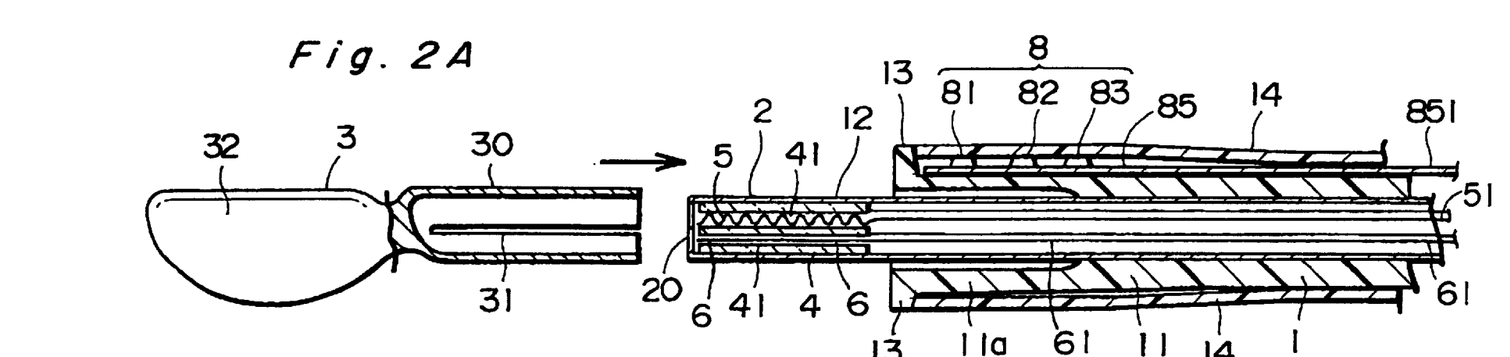
FIG. 2A is a magnified sectional view showing the heating portion of the wax spatula body in accordance with the embodiment of the present invention.

FIG. 2A is a sectional view showing a front half of the spatula body 10. At the front end of the grip portion 1, being cylindrical and formed of a synthetic resin, of the spatula body 10, the metal sheath 2 projects to form the heating portion 12 as described above. The metal sheath 2 is formed of a pipe made of copper, brass, aluminum or stainless steel, for example. The cylindrical ceramic insulator 4 is inserted into the front end of the sheath 2.

Four small holes 41 passing through the ceramic insulator 4 are formed therein. The ceramic insulator 4 is formed of an alumina-sintered body. A nichrome wire, having the shape of a spiral coil and used as a heating wire 5, is inserted into the two small holes 41 and 41 among the four small holes 41 of the ceramic insulator 4. Furthermore, an alumel-chromel wire used as the thermocouple 6 of the temperature sensor is inserted into the other two small holes 41 and 41.

Figure 2B:
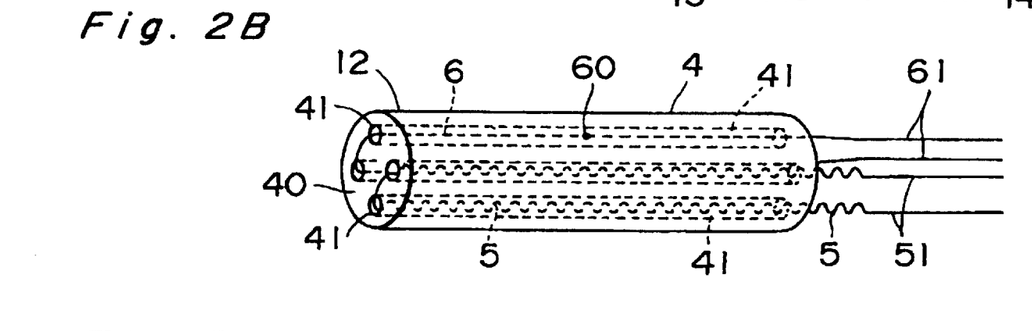
FIG. 2B is a perspective view showing a ceramic insulator for use in the wax spatula in accordance with the embodiment of the present invention.
Figure 2C:
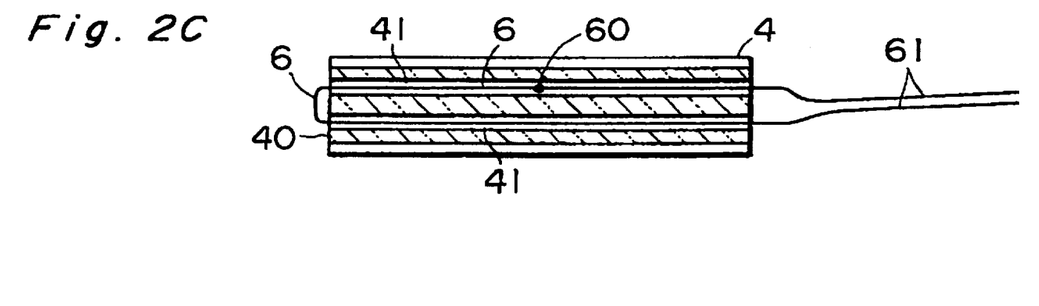
FIG. 2C is a partially sectional view of the ceramic insulator shown in FIG. 2B.

FIG. 2B is an external view showing the cylindrical ceramic insulator 4. FIG. 2C is a vertical sectional view taken on a plane including the center axes of the two small holes 41 and 41 through which the alumel-chromel wire passes. The heating wire 5 inserted from the grip portion 1 into the two small holes 41 and 41 in the insulator 4 is folded back at the end face 40 of the front end of the insulator 4. The above-mentioned thermocouple 6 inserted into the other two small holes 41 and 41 is also folded back in the same way at the end face 40 of the front end of the insulator 4. In this embodiment, the thermocouple 6 is disposed so that its junction point 60 (temperature measurement point) is positioned at a nearly central position inside the small hole 41 in the axial direction thereof.

The spatula portion 3 is connected to the front end of the metal sheath 2 used as the heating portion 12. The spatula portion 3, comprising the cylindrical socket 30 adapted to receive and engage the sheath 2 and a wax-molding portion 32 having the shape of a spatula or the like, is an integrated member formed of metal, such as brass. Slots 31 are provided in the socket 30 in the horizontal direction. The socket 30 is designed to be expandable around the exterior of the sheath 2 and elastically make contact therewith, thereby to ensure insertion and engagement.

Furthermore, as shown in FIGS. 2 and 4, the lead wires 51 of the heating wire 5 and the lead wires 61 of the thermocouple 6 are inserted into the hollow portion of the grip portion 1. These wires are extended from the rear end of the grip portion 1, pass through the inside of the cord 15 and are connected to the temperature controller 70.

Figure 3:
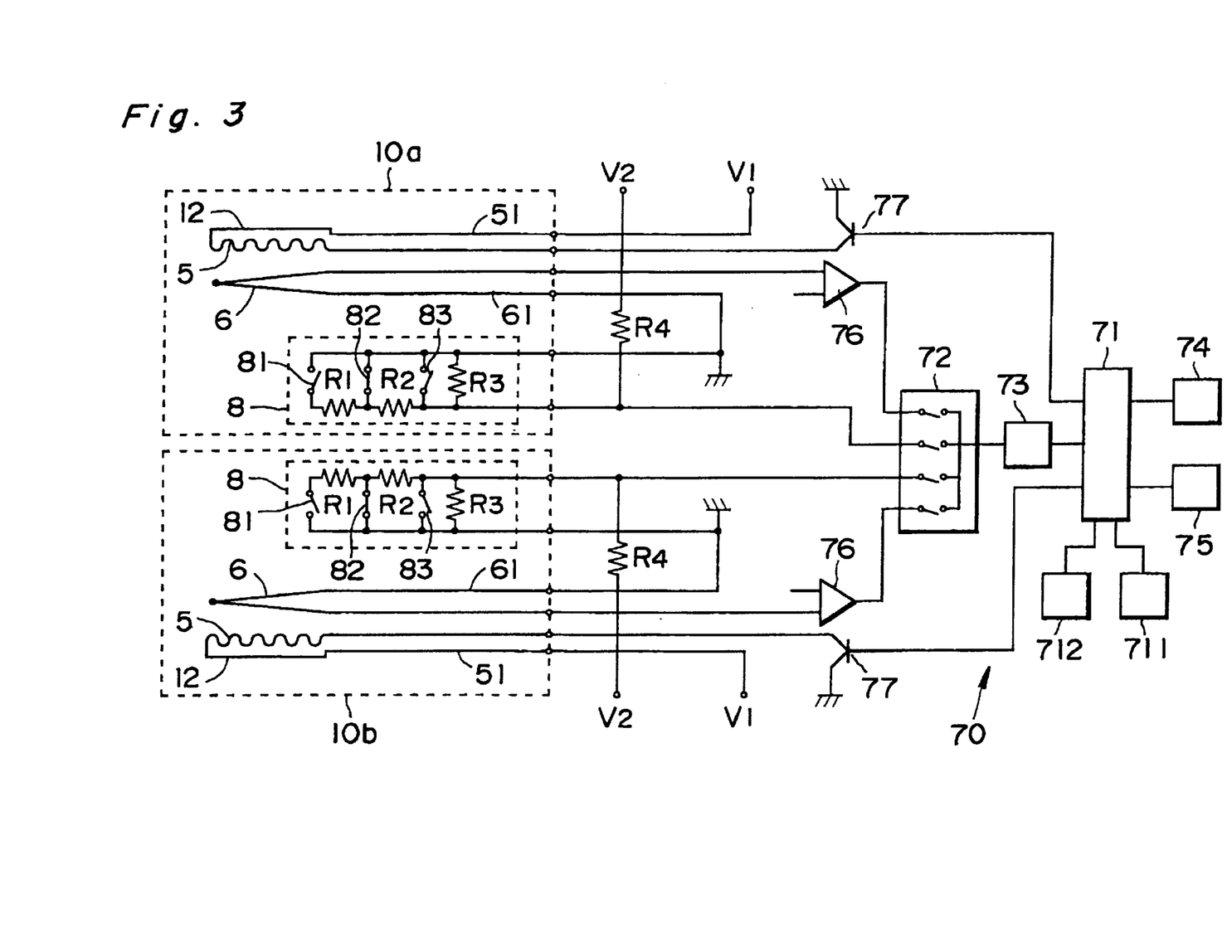
FIG. 3 is a block diagram of the temperature controller of the wax spatula apparatus in accordance with the embodiment of the present invention.

FIG. 3 is a block diagram of the computer-controlled temperature control system of the temperature controller 70. The temperature controller 70 controls two spatula bodies in the case of this example. The heating element 5 of the heating portion 12 of each of spatula bodies 10a and 10b is connected to a DC power source V1 and a current controller 77 (a transistor 77 in this example) in series. A CPU 71 controls the current controller 77.

As shown in FIG. 4, the operation panel of the temperature controller 70 includes a selection switch 74 used as preset temperature selection means and a preset temperature indicator 75 for indicating a preset temperature. These are connected to the CPU 71. The temperature-setting means can set a plurality of temperature levels. The temperature controller of this embodiment controls the temperature of the heating portion 12 at four levels. Referring to FIG. 4, the selection switch 74 used as the preset temperature selection means is used to select a temperature level. Four level selection switches 741a, 742a, 743a and 744a respectively corresponding to the four levels are provided for the spatula body 10a. In the same way, four level selection switches 741b, 742b, 743b and 744b respectively corresponding to the four levels are provided for the spatula body 10b.

Furthermore, preset temperature indicators 75a and 75b for the spatula bodies 10a and 10b respectively are disposed on the operation panel to indicate preset temperatures. The preset temperature indicator may directly indicate a preset temperature or may indicate a relative temperature ranging from 0 to 100 divisions obtained by dividing the difference between the ambient temperature and the maximum temperature into 100 equal divisions.

The temperature sensor 6 (the thermocouple in this embodiment) of the heating portion 12 is connected to the CPU 71 via an amplifier 76. The temperature-setting switch 8 secured to the grip portion 1 is connected to the temperature-setting portion inside the CPU 71. The output terminal of the amplifier 76 of the temperature sensor 6 and the temperature-setting switch 8 are connected to the CPU 71 via a multiplexer 72 and an AD converter 73.

An example of the circuit of the temperature-setting switch 8 is shown in FIG. 3. In the small switches 81, 82 and 83 of the temperature-setting switch 8, one of the terminals of each switch is connected to the grounding wire. The other terminals of the small switches are connected to one another via resistors R1 and R2, connected to the connection point of a grounded resistor R3 and a resistor R4 connected to a power source V2, and further connected to the AD converter 73 via the multiplexer 72. When one of the small switches 81, 82 and 83 is closed, a potential obtained by dividing V2 by the ratio of the resistance of the resistor R4 and the combined resistance of the other resistors depending on the switch operation is input to the A/D converter 73. As a result, a digitized signal is input to the CPU and the closed switch is identified. Since only the two lead wires are used, this circuit is advantageous in a case wherein the switches are mounted together with the resistors on the narrow printed-circuit board to be incorporated inside the spatula body. In this embodiment, the small switch 81 is used to raise the temperature of the spatula portion, the small switch 82 is used to turn off heating, and the small switch 83 is used to lower the temperature. With this configuration, the current preset temperature can be changed to a higher or lower temperature by operating the small switch 81 or 83.

When one of the levels 1 to 4 is selected by operating the corresponding selection switch 74, the CPU 71 controls the current controller 77 (turns on the current-controlling transistor 77) to energize the heating element 5 of the heating portion 12 so that the temperature is raised to the selected preset temperature level. The output of the temperature sensor 6 (the electromotive force of the thermocouple) disposed near the heating element 5 inside the heating portion 12 is amplified by the amplifier 76. The output is then digitized, input to the CPU 71 and converted into a temperature signal. The temperature signal is then compared with the specific temperature value selected from among the preset temperature levels. A comparison signal is obtained and the comparison signal controls the current controller 77 so that the temperature is maintained at the preset temperature or close thereto. When another preset temperature selection switch of the selection switch 74 is pushed, the temperature of the heating portion 12 is changed to the preset temperature corresponding to the selection switch.

When the setting of the currently preset temperature is desired to be changed to the setting of another preset temperature; the operator pushes the temperature-raising switch 81 or the temperature-lowering switch 83 of the temperature-setting switch 8 provided on the grip portion of the spatula body to raise or lower the currently preset temperature while the level selection switch having been selected currently remains selected. The preset temperature selected as described above is indicated on the indicator 75. While watching the temperature indication on the indicator, the operator pushes the temperature-raising switch 81 or the temperature-lowering switch 83 of the temperature-setting switch 8 to obtain the desired temperature. After the setting of the preset temperature is changed to the setting of the newly preset temperature as described above, the CPU compares the newly preset temperature with the actual temperature measured by the temperature sensor 6, and carries out temperature control by controlling the current controller 77 so that the actual temperature reaches the newly preset temperature immediately. The adjustable interval of the preset temperature levels should preferably be 1° C. or 3° C. to 5° C., as necessary.

Even during wax-molding work, the operator can easily operate the temperature-setting switch 8 by simply pushing the temperature-raising switch 81 or the temperature-lowering switch 83 of the temperature-setting switch 8 with the tip of one finger of the hand holding the spatula. After the setting is completed, the actual temperature of the heating portion 12 is maintained at the newly preset temperature immediately. For this reason, the operator can continue spatula work with almost no need for taking a break. As a result, the operator can fine adjust the temperature promptly to the temperature suited for the next operation while continuing the above-mentioned complicated operation.

Each of the selection switches should preferably be provided with an indication lamp to indicate the current temperature level.

In accordance with the present invention, the preset temperature for the spatula portion of the wax spatula body can be changed immediately to two or more temperature levels. Hence, the temperature during wax-molding work can be adjusted easily. Furthermore, the temperature can easily be changed immediately to a plurality of temperature levels required for the corresponding wax-molding processes. In particular, the preset temperature at each temperature level can be set as desired by-the temperature-setting means. In addition, the adjustment for changing or maintaining the temperature during use and the temperature during disuse can be carried out easily. Wax molding work can thus be carried out efficiently.

Furthermore, in accordance with the present invention, since the temperature-setting switch is disposed on the grip portion of the spatula body, the preset temperature can easily be changed immediately during complicated wax-molding work, and the efficiency of the wax-molding work can be raised significantly.

What is claimed is:

1. A dental wax spatula apparatus comprising:
    a spatula body having a heating portion, said heating portion accommodating an electric heating element and a temperature sensor;
    a wax-shaping spatula portion removably attached to said heating portion, said wax-shaping spatula portion being constructed and arranged to shape a dental wax model for casting a tooth array or a crown for dental prostheses; and
    a temperature controller for controlling a temperature of said wax-shaping spatula portion by supplying electric power to said electric heating element and by controlling an amount of the electric power supplied to said electric heating element in response to a temperature sensed by said temperature sensor, said temperature controller including
        (i) a preset temperature selection device for selecting a preset temperature for said wax-shaping spatula portion, and
        (ii) a temperature-setting device for independently and immediately setting a temperature of said wax-shaping spatula portion that is different from the preset temperature selected by said preset temperature selection device, said temperature-setting device including at least one temperature-setting switch for raising or lowering the temperature of said wax-shaping spatula portion as selected by said preset temperature selection device, with said at least one temperature-setting switch being secured to said spatula body so as to be operable by a fingertip of a hand which is holding said spatula body.

2. The dental wax spatula apparatus according to claim 1, wherein said preset temperature selection device is for selecting a preset temperature for said wax-shaping spatula portion from among a plurality of preset temperatures, and
    wherein said at least one temperature-setting switch for raising or lowering the temperature of said wax-shaping spatula portion as selected by said preset temperature selection device comprises a first temperature-setting switch for raising the temperature of said wax-shaping spatula portion as selected by said preset temperature selection device and a second temperature-setting switch for lowering the temperature of said wax-shaping spatula portion as selected by said preset temperature selection device.

3. The dental wax spatula apparatus according to claim 2, wherein said first temperature-setting switch and said second temperature-setting switch each comprise a push-button switch.

4. The dental wax spatula apparatus according to claim 2, wherein said spatula body further has a grip portion, with said heating portion being located at a front end of said grip portion, and with said first and second temperature-setting switches being secured to said spatula body by being secured to said grip portion so as to be operable by a fingertip of a hand which is holding said grip portion.

5. The dental wax spatula apparatus according to claim 4, wherein said preset temperature selection device includes a selection switch, and said preset temperature selection device is for selecting the preset temperature from among the plurality of preset temperatures by immediately selecting the preset temperature from among the plurality of preset temperatures via operation of said selection switch.

6. The dental wax spatula apparatus according to claim 5, wherein said temperature controller includes an operation panel, and said selection switch is on said operation panel.

7. The dental wax spatula apparatus according to claim 4, wherein said heating portion includes
    (i) a metal sheath having first and second ends, with said first end being secured to said grip portion,
    (ii) a ceramic insulator within said metal sheath at said second end of said metal sheath, said ceramic insulator having plural small holes extending therethrough with said temperature sensor extending through some of said plural small holes, and
    (iii) an electric heating wire extending through other of said plural small holes, with said electric heating element comprising said electric heating wire,
    wherein said wax-shaping spatula portion includes a socket such that said wax-shaping spatula portion is removably attached to said heating portion by having said second end of said metal sheath be removably received within said socket, and
    wherein leads of said electric heating wire and leads of said temperature sensor extend through said grip portion and are connected to said temperature controller.

8. The dental wax spatula apparatus according to claim 7, wherein said electric heating wire extends through said other of said plural holes by extending through a first of said plural holes and projecting therefrom at a first end of said ceramic insulator, and by extending through a second of said plural holes and projecting therefrom at a second end of said ceramic insulator, and
    wherein said temperature sensor comprises a wire which extends through said some of said plural holes by extending through a third of said plural holes and projecting therefrom at said first end of said ceramic insulator, and by extending through a fourth of said plural holes and projecting therefrom at said second end of said ceramic insulator.

9. The dental wax spatula apparatus according to claim 7, wherein said temperature sensor comprises a wire thermocouple having a temperature measurement point located within one of said some of said plural small holes near said electric heating wire extending through said other of said small holes.

10. The dental wax spatula apparatus according to claim 4, wherein said grip portion includes a flat portion on an outer periphery of said grip portion, and further comprising a circuit board secured to said flat portion and covered by a soft rubber protective cover that surrounds said grip portion, with said first and second temperature-setting switches being mounted on said circuit board.

11. The dental wax spatula apparatus according to claim 5, wherein said preset temperature selection device includes a selection switch, and said preset temperature selection device is for selecting the preset temperature from among the plurality of preset temperatures by immediately selecting the preset temperature from among the plurality of preset temperatures via operation of said selection switch.

12. The dental wax spatula apparatus according to claim 2, wherein said heating portion includes
    (i) a metal sheath having first and second ends, with said first end being secured to said grip portion,
    (ii) a ceramic insulator within said metal sheath at said second end of said metal sheath, said ceramic insulator having plural small holes extending therethrough with said temperature sensor extending through some of said plural small holes, and
    (iii) an electric heating wire extending through other of said plural small holes, with said electric heating element comprising said electric heating wire,
    wherein said wax-shaping spatula portion includes a socket such that said wax-shaping spatula portion is removably attached to said heating portion by having said second end of said metal sheath be removably received within said socket, and
    wherein leads of said electric heating wire and leads of said temperature sensor extend through said grip portion and are connected to said temperature controller.

13. The dental wax spatula apparatus according to claim 2, wherein said spatula body includes a flat portion on an outer periphery of said spatula body, and further comprising a circuit board secured to said flat portion and covered by a soft rubber protective cover that surrounds said spatula body, with said first and second temperature-setting switches being mounted on said circuit board.

14. The dental wax spatula apparatus according to claim 1, wherein said heating portion includes
    (i) a metal sheath having first and second ends, with said first end being secured to said spatula body,
    (ii) a ceramic insulator within said metal sheath at said second end of said metal sheath, said ceramic insulator having plural small holes extending therethrough with said temperature sensor extending through some of said plural small holes, and
    (iii) an electric heating wire extending through other of said plural small holes, with said electric heating element comprising said electric heating wire,
    wherein said wax-shaping spatula portion includes a socket such that said wax-shaping spatula portion is removably attached to said heating portion by having said second end of said metal sheath be removably received within said socket, and
    wherein leads of said electric heating wire and leads of said temperature sensor extend through said grip portion and are connected to said temperature controller.

15. The dental wax spatula apparatus according to claim 14,
    wherein said electric heating wire extends through said other of said plural holes by extending through a first of said plural holes and projecting therefrom at a first end of said ceramic insulator, and by extending through a second of said plural holes and projecting therefrom at a second end of said ceramic insulator, and
    wherein said temperature sensor comprises a wire which extends through said some of said plural holes by extending through a third of said plural holes and projecting therefrom at said first end of said ceramic insulator, and by extending through a fourth of said plural holes and projecting therefrom at said second end of said ceramic insulator.

16. The dental wax spatula apparatus according to claim 15, wherein said temperature sensor comprises a wire thermocouple having a temperature measurement point located within one of said some of said plural small holes near said electric heating wire extending through said other of said small holes.

17. The dental wax spatula apparatus according to claim 1, wherein said preset temperature selection device includes a selection switch, and said preset temperature selection device is for selecting a preset temperature for said wax-shaping spatula portion by immediately selecting the preset temperature from among a plurality of preset temperatures via operation of said selection switch.

18. The dental wax spatula apparatus according to claim 17, wherein said temperature controller includes an operation panel, and said selection switch is on said operation panel.

19. The dental wax spatula apparatus according to claim 1, wherein said spatula body further has a grip portion, with said heating portion being located at a front end of said grip portion, and with said at least one temperature-setting switch being secured to said spatula body by being secured to said grip portion so as to be operable by a fingertip of a hand which is holding said grip portion.

20. The dental wax spatula apparatus according to claim 1, wherein said temperature sensor comprises a wire thermocouple.

21. The dental wax spatula apparatus according to claim 1, wherein said spatula body includes a flat portion on an outer periphery of said spatula body portion, and further comprising a circuit board secured to said flat portion and covered by a soft rubber protective cover that surrounds said spatula body, with said at least one temperature-setting switch being mounted on said circuit board.

22. The dental wax spatula apparatus according to claim 1, wherein said at least one temperature-setting switch comprises a push-button switch.

* * * * *